(12) United States Patent
Novikov et al.

(10) Patent No.: US 8,221,734 B2
(45) Date of Patent: Jul. 17, 2012

(54) SELF-HEATING SHAVING COMPOSITIONS

(75) Inventors: Alexander Novikov, Cincinnati, OH (US); Uday Marutirao Patil, Mason, OH (US); Robert John Willicut, Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 308 days.

(21) Appl. No.: 12/555,406

(22) Filed: Sep. 8, 2009

(65) Prior Publication Data
US 2010/0086509 A1    Apr. 8, 2010

Related U.S. Application Data

(60) Provisional application No. 61/095,194, filed on Sep. 8, 2008.

(51) Int. Cl.
| | |
|---|---|
| *A61K 8/19* | (2006.01) |
| *A61Q 9/00* | (2006.01) |
| *A61K 9/12* | (2006.01) |
| *A61K 8/72* | (2006.01) |
| *A61K 8/30* | (2006.01) |
| *A61Q 5/00* | (2006.01) |
| *A61Q 7/00* | (2006.01) |
| *B65D 5/72* | (2006.01) |
| *B65D 25/40* | (2006.01) |
| *B65D 35/38* | (2006.01) |
| *C09K 3/00* | (2006.01) |
| *C07C 51/50* | (2006.01) |
| *C11B 5/00* | (2006.01) |
| *C11D 1/28* | (2006.01) |

(52) U.S. Cl. ...... 424/73; 424/44; 424/70.11; 424/70.13; 424/70.19; 424/70.22; 424/70.24; 424/70.31; 222/491; 222/575; 252/183.11; 252/183.12; 554/2; 554/85

(58) Field of Classification Search ............... 424/73, 424/44, 70.11, 70.13, 70.19, 70.22, 70.24, 424/70.31; 222/491, 575; 252/183.11, 183.12; 554/2, 85
See application file for complete search history.

(56) References Cited

U.S. PATENT DOCUMENTS
3,585,982 A   6/1971   Hollinshead
4,088,751 A * 5/1978   Kenkare et al. ............ 424/47
(Continued)

FOREIGN PATENT DOCUMENTS
FR    2060247    6/1971
(Continued)

OTHER PUBLICATIONS
PCT International Search Report with Written Opinion in corresponding Int'l appln. PCT/US2009/056186 dated Mar. 30, 2011.

*Primary Examiner* — Johann Richter
*Assistant Examiner* — Jane C Oswecki
(74) *Attorney, Agent, or Firm* — Jay A. Krebs; Ronald T. Sia; Mark A. Charles

(57) ABSTRACT

Non-pressurized shaving compositions are described that provide a warm/hot sensation during use as the result of an exothermic redox reaction. The compositions are post-foaming via nascent gas release in situ due to the generation of carbon dioxide. The carbon dioxide induced foam is maintained for several minutes after the compositions are dispensed, whereby the compositions are capable of providing both a warm sensation and sustained lather, a balance which heretofore has been a significant challenge.

16 Claims, 1 Drawing Sheet

U.S. PATENT DOCUMENTS

| | | | |
|---|---|---|---|
| 5,223,245 A * | 6/1993 | Ibrahim et al. | 424/44 |
| 5,233,245 A * | 8/1993 | Romano et al. | 327/553 |
| 6,696,054 B1 | 2/2004 | Falanga | |
| 2004/0047830 A1 | 3/2004 | Goldberg et al. | |
| 2004/0166085 A1 | 8/2004 | Manivannan et al. | |
| 2004/0166086 A1 | 8/2004 | Manivannan et al. | |
| 2006/0029565 A1 | 2/2006 | Xu et al. | |
| 2006/0029566 A1 | 2/2006 | Xu et al. | |
| 2006/0228319 A1 * | 10/2006 | Vona et al. | 424/70.13 |
| 2008/0178898 A1 * | 7/2008 | Aubert et al. | 132/200 |

FOREIGN PATENT DOCUMENTS

| | | | |
|---|---|---|---|
| JP | 2005170861 A | * | 6/2005 |
| JP | 20050170861 A | * | 6/2005 |

* cited by examiner

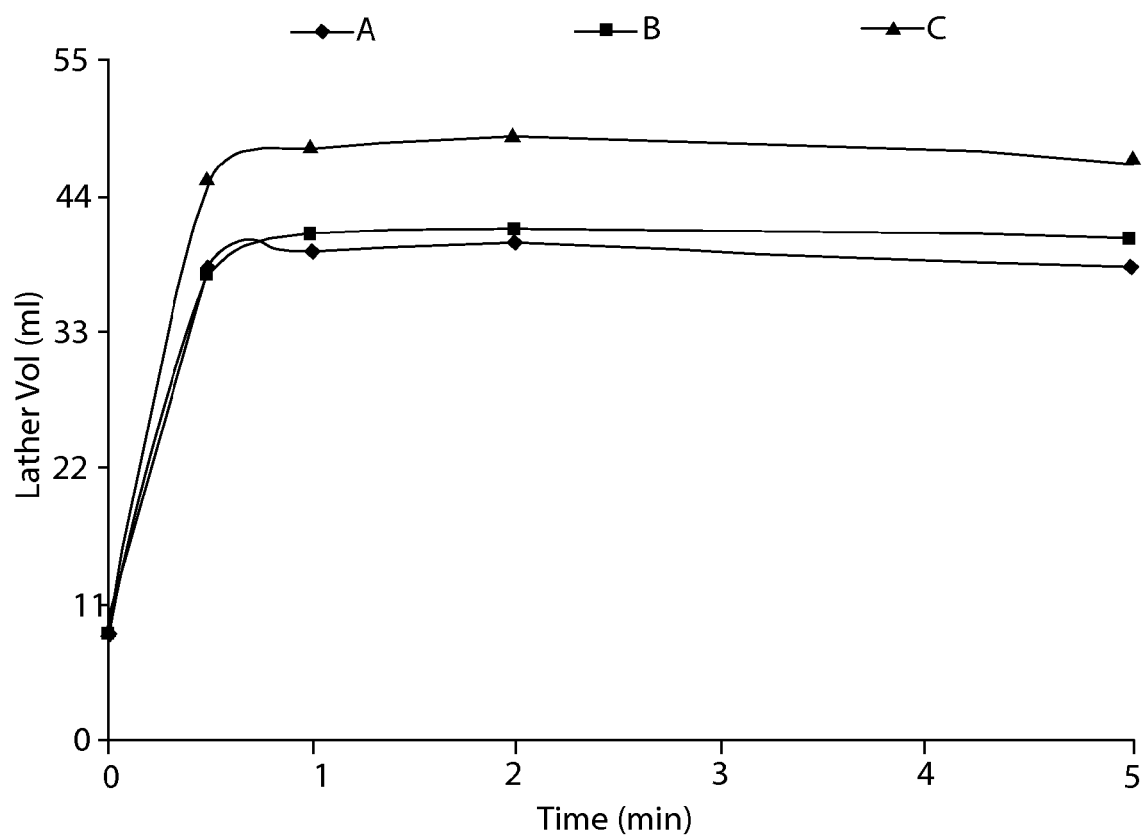

SELF-HEATING SHAVING COMPOSITIONS

CROSS REFERENCE TO RELATED APPLICATION

This application claims the benefit of U. S. Provisional Application No. 61/095,194, filed Sep. 8, 2008.

FIELD OF THE INVENTION

The present invention is directed to non-aerosol shaving products that employ technology to provide both heat and lather during use.

BACKGROUND OF THE INVENTION

The use of reactive chemistry to create self-heating personal care compositions is known. The general approach involves employing a multi-chambered package with one chamber holding an oxidative phase and another chamber holding a reductive phase. Dispensing and mixing the two phases results in heat development through a chemical reaction between the oxidative phase and reductive phase.

Shaving compositions is one art area that has experienced significant development of self-heating chemistries. The sensation of warmth on skin prior to and/or during shaving can be perceived as highly beneficial by users of exposed blade razors. Consumers believe that heat can accomplish one or more of the following: open pores, soften skin and beard hair, provide a closer and more comfortable shave, reduce irritation, and leave skin refreshed and protected.

One prior self-heating shaving composition featured a non-aerosol formulation that employed separate non-ionic emulsion bases containing a reductant and oxidant, respectively. By virtue of the non-ionic base and no gas being involved, the formulation was essentially a non-lathering shave product. Despite the benefits of heat associated with the formulation, the majority of consumers still prefer lathering shave preps. Thus, developing a shaving product that combines the sensation of warmth and perceivable lather would be advantageous. The attempts to date however have not been optimal. For example, one prior attempt has employed conventional soap-based formulas pressurized in an aerosol package containing a volatile hydrocarbon propellant. But several disadvantages are realized with this approach, including VOC concern, fast heat dissipation, harshness of the soap base, and complicated/expensive aerosol packaging. Another prior attempt involved incorporating volatile hydrocarbons or fluorinated hydrocarbons in water-base emulsions which would volatilize upon spreading the composition onto one's skin. These formulations proved however to be highly unstable and prone to losing hydrocarbons during storage.

Accordingly, there is room for improvement in the development of a shaving product that adequately provides both heat and sustained lather.

SUMMARY OF THE INVENTION

The present invention is directed to self-heating shaving products that feature lather produced by nascent gas release in situ when mixing reductant and oxidant phases. The shaving products employ either a multi-chambered container or two separate containers that hold and dispense a first composition and a second composition. The first composition comprises a reducing agent and a carbon dioxide source, and the second composition comprises an oxidizing agent. The first composition is preferably formulated at a pH of from about 8.5 to about 10.5 to ensure stability of the carbon dioxide source. And the second composition is preferably formulated at a pH of from about 2.8 to about 3.8. When the first and second compositions are combined an exothermic redox reaction occurs to produce heat. Another result of the redox reaction employed in this invention is the formation of acid. As the reaction is completed, the high pH associated with the first composition drops, which in turn drives the release of carbon dioxide to produce the initial lather/foam. To sustain and/or accentuate the initial lather, systems comprising surfactants, opacifiers, and/or polymers are employed.

BRIEF DESCRIPTION OF THE DRAWING

The FIGURE is a chart illustrating lather dynamics (first 5 minutes) with different reductant formulations.

DETAILED DESCRIPTION OF THE INVENTION

The present invention may be understood more readily by reference to the following detailed description of illustrative and preferred embodiments. It is to be understood that the scope of the claims is not limited to the specific ingredients, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

All percentages and ratios used herein are by weight of the first, second or mixed composition, and all measurements made are at 25° C., unless otherwise designated.

The self-heating shaving products comprise a first composition containing a reducing agent and second composition containing an oxidizing agent, which when combined into a mixed composition generate heat from the exothermic redox reaction. The first composition further comprises a source for generating carbon dioxide to foam or lather the mixed composition. The first and second compositions are kept separate from one another prior to use, preferably through employment of a multi-chambered container/dispenser or two separate containers/dispensers. The containers/dispensers employed for the shaving compositions of the present invention do not require a volatile propellant and are preferably not pressurized in any way. Furthermore, prior to being dispensed, the first and second compositions are maintained at substantially atmospheric pressure.

Each of the first and second compositions comprises oil-in-water emulsions that could independently be used as a shaving preparation without significant skin irritation. The oil phase of the respective emulsions can include any desired emollient that is safe for use in topical formulas, is compatible with other ingredients of the compositions, and provides the desired aesthetics. Suitable emollients include mineral oil, petrolatum, squalane/squalene, hydrogenated/unsaturated polyisobutene and mixtures thereof. Exemplary compositions contain from about 0.25% to about 15% of the emollient, from about 0.5% to about 12% of the emollient, or from about 0.75% to about 8% of the emollient.

The first composition comprises a reducing agent. A representative, non-limiting list of suitable reducing agents includes thiosulfate and sulfite compounds, such as sodium sulfite, sodium thiosulfate (e.g., sodium thiosulfate pentahydrate), ammonium thiosulfate, potassium thiosulfate, and thiourea; and compounds with a thiourea backbone, such as 1,5-diethyl-2-thiobarbituric acid or its derivatives, or ascorbic acid. Mixtures of these reducing agents, and other suitable reducing agents, may also be used. In some embodiments, the first composition employs the reducing agent at concentrations from about 2% to about 10%, preferably from about 3% to about 8%, by weight of the first composition.

A carbon dioxide source is also included in the first composition. The carbon dioxide source can be, for example, carbonate or bicarbonate salts of alkaline or alkaline earth metals, such as sodium, potassium, calcium and magnesium carbonates, and sodium and potassium bicarbonates. Mixtures of these materials can be used, as well as other carbon dioxide sources generally known to the skilled artisan. The carbon dioxide source is included in some first composition embodiments at concentration levels of from about 1% to about 10%, from about 2% to about 7%, and from about 3% to about 5%, by weight of the first composition.

The first composition is preferably formulated to a pH of from about 8.5 to about 10.5 to ensure stability of the carbon dioxide source during storage. Materials that can be used to adjust the pH include, for example, sodium and potassium hydroxide, calcium oxide, triethanolamine, and sodium and potassium carbonate. Such pH adjusters can be employed at a level for example of from about 2% to about 8%, or from about 3% to about 5%, by weight of the first composition.

The second composition comprises an oxidizing agent. Suitable oxidizing agents include, but are not limited to, peroxides, such as hydrogen peroxide (typically added as a 35% solution), benzoylperoxide, peroxomonosulfate, peroxodisulfate, urea hydrogen peroxide, and t-butyl peroxide. In some embodiments, the second composition may include from about 2% to about 10% of the oxidizing agent. In certain embodiments, the second composition can include from about 12% to about 16% of an oxidizing agent, such as hydrogen peroxide (35%) (which corresponds to about 4% to about 6% $H_2O_2$ active).

The second composition is preferably formulated to a pH of from about 2.8 to about 3.8, or from about 3.0 to about 3.6. The reason for this preferred range is three-fold: 1) to achieve a final pH of from about 5 to about 7 (or from about 6.0 to about 6.8) of the stoichiometric mixture of the first and second compositions whereby heat production and gas release are satisfactory; 2) to enhance storage stability of the oxidizing agent; and 3) to mitigate the potential for skin irritation when dispensing ratios of the first and second compositions are off target. The pH adjusters of the second composition are mineral acids (e.g., phosphoric acid), at a concentration of 0.25% to 1.5%, and preferably 0.75% to 1.0%. Acid can be partially neutralized by employing sodium tetraborate at around 1-2.5%, so that a pH of 3.0 to 3.4 is achieved. Other pH adjusters can be used, including, for example, disodium or dipotassium phosphate, calcium or magnesium oxide or hydroxide.

As noted above, the first and second compositions are kept separate from one another prior to use. The volumes of the first and second compositions are included in separate containers or separate chambers of single containers so that they can be dispensed in appropriate relative amounts to provide a stoichiometric exothermic reaction when mixed. As the redox reaction results in the formation of acid, the high pH associated with the first composition drops, which in turn drives the release of carbon dioxide to produce the initial lather/foam. Lather in some of the embodiments typically starts forming about 5-10 seconds after mixing the first and second compositions, with temperature rising to about 35-40° C. during this time frame. The temperature continues to rise, reaching a maximum temperature of about 50-55° C. within 50-60 seconds after mixing and remains at that level for another 10-20 seconds. The lather/foam volume associated with the mixed composition can increase to greater than 5 times the initial dispensed volume. The lather/foam volume at around one minute after dispensing however is not sustained as the mixed composition is spread onto one's skin because the escaping carbon dioxide is not trapped to a significant extent by the mixed emulsion. The lather/foam volume upon spreading can be ⅓ of the peak volume achieved around one minute after dispensing and mixing the first and second compositions. Applicant however discovered a number of different techniques to sustain lather/foam volume, which are discussed in more detail below.

Particular surfactant systems for each of the first and second compositions is one technique discovered by the Applicant to sustain the carbon dioxide induced lather/foam. Primary surfactants for the first composition include mild non-ionic surfactants free from polyethylene oxides, such as, for example, polyglycerol fatty esters, glycosyl ethers, and sugar esters. Exemplary polyglycerol fatty esters include decaglyceryl dipalmitate, hexaglyceryl myristate, decaglyceryl laurate, hexaglyceryl laurate, and triglyceryl stearate. A representative, non-limiting list of suitable glycosyl ethers includes cetearyl polyglucoside, behenyl polyglucoside, myristyl polyglucoside, and cocoyl polyglucoside. Suitable sugar ester include, but are not limited to, sucrose esters, such as sucrose monostearate and sucrose distearate; and sorbitan esters, such as sorbitan monostearate, sorbitan palmitate, sorbitan oleate, sorbitan sesquioleate, and sorbitan isostearate or esters of mixed structure (e.g., PEG-3 methylglucose distearate). These primary surfactants may be employed at concentration levels of from about 2-8% or 3-5%, by weight of the first composition.

To boost the initial carbon dioxide induced lather/foam, one or more anionic surfactants can be formulated into the first composition in addition to the non-ionic surfactants discussed above. The one or more anionic surfactants are generally included at a total concentration of up to about 5%, by weight of the first composition. Exemplary anionic surfactants include fatty acyl sulfosuccinates, sarcosinates and lactylates. Di-sodium laureth-2 sulfosuccinate, sodium lauroyl sarcosinate and sodium lauroyl lactylate are some of the preferred anionic surfactants.

Exemplary surfactant systems for the second composition include a combination of ethers of fatty alcohols and polyoxyethylene with an ethylene oxide chain from 2 to 100 and fatty alkyl chain from 12 to 24. These surfactants are believed to be stable in the presence of the oxidizing agent, and be able to provide a stable shaving composition with desirable viscosity, aesthetics and rinsing properties. One preferred combination is a blend of derivatives with shorter and longer ethylene oxide chains. In certain embodiments, the second composition may include form about 2% to about 8% (or from about 2% to about 6%) of a non-ionic surfactant. In other embodiments, the second composition may include from about 2% to about 6%, preferably from about 3% to about 5%, of a shorter polyethylene oxide chain length non-ionic surfactants, such as Steareth-2. Additionally, the second composition may include from about 1% to about 4%, preferably from about 1.5% to about 3%, of a long polyethylene oxide chain length non-ionic surfactant, such as Steareth-21. In some embodiments, the second composition can include form about 1% to about 6% of one non-ionic surfactant, and from about 1% to about 6% of another, different non-ionic surfactant.

To stabilize the carbon-dioxide induced foam, Applicant discovered that materials can be employed to increase the viscosity of the liquid surrounding individual bubbles. These materials may include, for example, amphoteric surfactants, such as Cocamidopropyl Betaine or Cocamidopropyl Hydroxysultaine; alkoxylated fatty amides, such as PPG-2 Hydroxyethyl Cocamide, PPG-2 Hydroxyethyl Coco/Isostearamide or PPG-3 Hydroxyethyl Soyamide; or silicone ethers, such as PEG-12 Dimethicone. When employed, these materials are generally included at a level of from about 0.5% to about 3.5%, and preferably from about 1.5% to about 2.0%.

Certain acidic polysaccharides (e.g., xanthan gum, alginates) can be employed to provide a negative charge to help prevent fusion of adjacent foam bubbles by means of electrostatic repulsion. By virtue of its highly pseudoplastic behavior, inclusion of xanthan gum can also increase the integrity of residual film of the mixed composition on one's skin.

Opacity is a desired property of lathering shave preparations since it can help with tracking blade strokes on the skin, and since it provides a confidence level that a protective residual film that exists between the blade and the skin. Using surfactants with long, saturated fatty chains, such as $C_{16}$-$C_{22}$ can provide such an opacifying effect. Examples of these types of surfactants include Steareth-2, Steareth-21, Cetearyl Glucoside, Arachidyl Glucoside, Sucrose Stearate and Sucrose Distearate, and PEG-3 Methylglucose Distearate. Imparting an opacifying effect can also be achieved by adding specific substances selected from the group comprising long chain fatty alcohols (e.g., cetearyl, stearyl, arachidyl alcohol); fatty esters (e.g., cetearyl stearate, cetearyl octanoate, cetyl palmitate, stearyl behenate, glyceryl distearate, glycol stearate, glycol distearate, PEG-3 Distearate); hydrocarbon waxes; and metal oxides, such as titanium dioxide, zinc oxide and magnesium oxide alone or in combination with a mica carrier. Other materials that can impart opacity can also be employed.

The rate of carbon dioxide release may also be manipulated to help sustain the lather/foam volume. This can be accomplished by increasing the pH of the mixed composition to a level of from about 6.2 to about 6.8. Increasing the level of alkaline (e.g., triethanolamine) or buffering salts (e.g., bicarbonates) can result in a higher mixed composition pH.

Bulking materials can be employed to further improve quality of the foam and provide more comfortable shaving. A representative, non-limiting list of suitable bulking materials includes clays, such as sodium potassium aluminum silicate; modified polysaccharides, such as hydroxypropyl starch phosphate and aluminum starch octenyl succinate. By way of example only, the optional bulking materials can be included at a concentration of level of 0.5-3% or 1-2%.

Several other optional ingredients can be included in one or both of the first composition and the second composition. For example, film-forming materials can be used to impart lubricity. Suitable film-forming materials include, but are not limited to, acrylamide/sodium acrylate/acrylic acid copolymers, sodium polyacrylate, chitosan derivatives (e.g., chitosan lactate or glycolate), associative thickeners (e.g., Polyether-1), natural waxes (e.g., beeswax, candelilla wax hydrocarbons and canauba acid wax), hydrocarbon polymers (e.g., petrolatum, mineral oil, squalane or polyisobutene), and hydrogenated vegetable oils (e.g., hydrogenated castor oil or hydrogenated olive oil). Such film-forming materials can be included at 1-10%.

To obtain certain targeted heat profiles, it may be advantageous to include a catalyst in the shaving composition. The catalyst is selected to catalyze the exothermic reaction, without deleterious effects on the skin or on the properties of the shave cream. The catalyst is generally included in the first composition that includes the reducing agent. Suitable catalysts for the exothermic reaction include sodium molybdate (e.g., sodium molybdate dihydrate), potassium molybdate, ammonium molybdate, sodium tungstate, potassium tungstate, and mixtures thereof. The first composition generally includes 0.1% to about 1.5%, preferably about 0.2% to about 1.0%, of the catalyst.

If the exothermic reaction generates an acid, as the reaction of the oxidizing and reducing agents discussed above will generally do, it is preferred that the first composition also include a neutralizing agent (a neutralizer). The neutralizing agent is selected and provided in a sufficient amount to neutralize enough of the acid so that the exothermic reaction is complete and the shaving composition will not irritate the user's skin. Preferably, substantially all of the acid is neutralized. Suitable neutralizing agents include, for example, triethanolamine, oxides (e.g., metal oxides), hydroxides (e.g., metal hydroxides), and metal carbonates, such as carbonates of alkaline metals (e.g., sodium, potassium), alkaline-earth metals (e.g., magnesium, barium), or transition metals (e.g., zinc). For example, the neutralizing agent may include calcium oxide, potassium hydroxide, sodium hydroxide, potassium bicarbonate, sodium bicarbonate or aluminum hydroxycarbonate. In some embodiments, the shaving composition (preferably the first composition) can include from about 0.5% to about 10% of such a neutralizer. For example, the first composition can include about 1% calcium oxide or about 4% triethanolamine.

The shaving composition may also contain other optional ingredients, including, for example, fragrances, colorants, skin-soothing agents, beard wetting agents, skin conditioning (e.g., exfoliating, moisturizing) agents (e.g., vitamin precursors and derivatives such as, for example, vitamins A, C and E, aloe, allantoin, panthenol, alpha-hydroxy acids, beta-hydroxy acids, phospholipids, triglycerides, botanical oils, amino acids), humectants (e.g., glycerin, sorbitol, pentylene glycol), phosphorus lipids (used, e.g., to encapsulate skin conditioning agents), antioxidants, preservatives, and other such ingredients. It may be desirable to include colorants in one or both of the first and second composition so that the compositions have different appearances. The contrast in appearance can help a user to mix the two compositions together upon dispensing so that an optimal level of heat and lather can be generated prior to and during use of the shaving composition.

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

First Composition Examples Comprising Reducing Agent (values by weight %)

| Ingredients | 1 | 2 | 3 | 4 | 5 | 6 | 7 | 8 |
|---|---|---|---|---|---|---|---|---|
| Cetearyl Glucoside | 0.5 | | | | | 0.8 | 1.0 | 1.0 |
| Sucrose Stearate | 1.5 | 2.0 | 2.0 | 2.0 | 1.5 | 1.5 | 1.5 | 1.5 |
| Decaglyceryl-6 Palmitate | | 3.0 | 3.0 | 3.0 | 2.0 | | | |
| PPG-2 Hydoxyethyl Coco/Isostearamide | | 1.5 | 1.5 | 2.0 | 1.5 | 2.0 | | 2.0 |
| Cocamidopropyl Betaine | 3.0 | | | | | | 2.0 | |
| Sodium Lauroyl Lactylate | 1.5 | | | | | | | |
| Di-sodium Laureth-2 Sulfosuccinate | | | | 3.0 | 2.0 | 3.0 | 3.0 | 3.0 |
| Sodium Myristoyl Sarcosinate | | | | | 3.0 | | | |
| Cetearyl Alcohol | 2.4 | 4.0 | 4.0 | 4.0 | 3.0 | 4.5 | 4.5 | 4.5 |
| Microcrystalline Wax | 1.0 | | | | | | | |
| Petrolatum | 2.0 | | | | | | | |
| Hydrogenated Castor Oil | | 1.5 | 1.5 | 1.5 | 1.0 | 1.5 | 1.5 | 1.5 |
| Polyisobutene & Polysorbate-20 & Polyacrylate-13 | 1.0 | 1.0 | 1.5 | 1.5 | 1.0 | 1.0 | 0.5 | |
| Polyether-1 | 0.5 | | | | | | | |
| Xanthan Gum | | | | | | 0.4 | 0.5 | 0.5 |
| Propyleneglycol Alginate | | | | 0.5 | 1.0 | 0.8 | | |
| Hydropropyl Starch Phosphate | | | 2.0 | 1.5 | 0.8 | 0.8 | 1.5 | 1.5 |
| Sodium Thiosulfate | 6.5 | 6.5 | 6.5 | 6.5 | 6.5 | 6.5 | 6.5 | 6.5 |
| Sodium Molybdate | 0.7 | 0.7 | 0.7 | 0.7 | 0.7 | 0.7 | 0.7 | 0.7 |
| Triethanolamine | 4.0 | 3.0 | 6.0 | 4.0 | 5.0 | 4.0 | 4.0 | 4.0 |
| Sodium Bicarbonate | | | | | | 3.0 | 3.0 | 4.0 |
| Potassium Bicarbonate | 3.0 | 3.0 | 3.0 | 2.0 | 3.0 | | | |
| Titanium Dioxide | | | | | 0.3 | | 0.4 | 0.4 |
| Titanium Dioxide and Mica | | | | | | 2.0 | | |
| Perfume | 2.0 | 2.0 | 2.0 | 2.0 | 2.0 | 1.5 | 2.0 | 2.0 |
| Dye Solution, 1% | 0.6 | 0.4 | 0.3 | 0.3 | 0.2 | | 0.05 | 0.05 |
| Water | Q.S. | Q.S. | Q.S. | Q.S. | Q.S. | Q.S. | Q.S. | Q.S. |

The above first composition examples can be made as follows: Dissolve the water-soluble components of the aqueous phase in water with adequate stirring and bring solution to 80° C. Add hydrophobic materials, such as the fatty alcohols, waxes, hydrocarbons, oils, and co-surfactants to the aqueous solution while continuing to stir. Heat the solution up to 85° C., add the non-ionic emulsifier, and then agitate at an increased speed for about 20 minutes. Cool and continue to stir. Add the neutralizer and anionic surfactant. Homogenize the batch at 68-70° C. using immersion or external homogenizer. Add the reducing and catalyst salts at 55-58° C. The polymer/thickener if needed can then be added and mixed in thoroughly. Add the carbon dioxide source to the batch when the batch is at a temperature below 45° C. Add fragrance and dye at 40° C. Homogenize the batch again for 1½ to 2 minutes to create a smooth cream consistency, having a target final viscosity of 35,000-65,000 cst using an RVT spindle #6 at 1 minute and 10 rpm.

Second Composition Examples Comprising Oxidizing Agent (values by weight %)

| Ingredients | 1 | 2 | 3 | 4 | 5 |
|---|---|---|---|---|---|
| Steareth-2 | 4.2 | 4.2 | 4.6 | 4.2 | 4.2 |
| Steareth-21 | 1.8 | 1.8 | 2.0 | 1.8 | 1.8 |
| Cetearyl Alcohol | 2.4 | 2.8 | 2.7 | 2.4 | 3.0 |
| Microcrystalline Wax | | | | 1.0 | |
| Polyisobutene | | | 2.9 | | |
| Petrolatum | | | | 2.0 | |
| Hydrogenated Castor Oil | 2.9 | 2.4 | | | |
| Beeswax | | | | | 2.0 |
| Polyisobutene & Polysorbate-20 & Polyacrylate-13 | | | | 1.0 | 0.5 |
| Polyethylene & PTFE | | | | | 0.5 |
| Titanium Dioxide & Mica | | | | | 2.0 |
| Phosphoric Acid | | | | 1.12 | 1.12 |
| Sodium Borate | | | | 1.8 | 1.8 |
| Hydrogen Peroxide | 4.0 | 4.0 | 4.0 | 4.0 | 4.0 |
| Dye Solution, 1% | | | 0.4 | | |
| Water | Q.S. | Q.S. | Q.S. | Q.S. | Q.S. |

The above second composition examples can be made as follows: Dissolve water-soluble materials in water to create aqueous phase and heat to 80° C. The oil soluble materials are then added with agitation. Add the non-ionic emulsifier with increased agitation and mix for 20 minutes at 85° C. Cool the mixture to 65° C. and homogenize briefly. Next, add the pH adjuster/buffering agent and then the phosphoric acid. Cool mixture to 40-42° C. and then add the hydrogen peroxide. The polymer/thickener, if one is desired, can then be added. Homogenize the final mixture at 38-40° C. to a smooth cream consistency, having a target final viscosity of 35,000-55,000 cst using an RVT spindle #6 at 1 minute and 10 rpm.

Three samples of first and second compositions, as described herein, were made and evaluated for foam/lather sustainment upon dispensing and mixing the two compositions. The FIGURE illustrates the foam volume dynamics beginning at time zero and extending out to 5 minutes. As one can see from the FIGURE, the samples substantially maintained the level of foam from a 30 second time measurement point to a five minute time measurement point.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A self-heating shaving product, comprising:
   (a) a container comprising a first chamber and a distinct second chamber;
   (b) a first composition disposed in the first chamber, the first composition comprising a reducing agent and a carbon dioxide source, the first composition having a pH of from about 8.5 to about 10.5; and
   (c) a second composition disposed in the second chamber, the second composition comprising an oxidizing agent, the second composition having a pH of from about 2.8 to about 3.8;
   (d) a non-ionic glycoside-based surfactant included in at least one of the first composition and the second composition;
   (e) an anionic surfactant included in at least one of the first composition and the second composition; and
   (f) an acidic polysaccharide included in at least one of the first composition and the second composition,
   wherein the oxidizing agent and the reducing agent are selected and being present in such proportion to provide a stoichiometric exothermic reaction and a drop in the pH of the first composition driving the release of carbon dioxide upon mixing of the first composition and the second composition resulting in a stoichiometric mixture having a pH of from about 5 to about 7.

2. The product of claim 1, wherein the non-ionic glycoside-based surfactant comprises fatty alkyl glycoside ether.

3. The product of claim 1, wherein the non-ionic glycoside-based surfactant comprises cetearyl glucoside.

4. The product of claim 1, wherein the non-ionic glycoside-based surfactant comprises fatty acyl glycoside ester.

5. The product of claim 1, wherein the non-ionic glycoside-based surfactant comprises sucrose stearate.

6. The product of claim 1, wherein the first composition further comprises an anionic surfactant.

7. The product of claim 1, wherein the anionic surfactant comprises disodium laureth-2 sulfosuccinate.

8. The product of claim 1, wherein the acidic polysaccharide comprises xanthan gum.

9. The product of claim 1, wherein the acidic polysaccharide comprises propyleneglycol alginate.

10. The product of claim 1, wherein a stoichiometric mixture of the first composition and the second composition has a pH of from about 6 to about 6.5.

11. The product of claim 1, wherein the container is not pressurized, and the first and second compositions are maintained at atmospheric pressure.

12. A self-heating shaving product, comprising:
   (a) a container comprising a first chamber and a distinct second chamber;
   (b) a first composition disposed in the first chamber, the first composition comprising a reducing agent, a non-ionic glycoside-based surfactant, an anionic surfactant, and a carbon dioxide source, the first composition having a pH of from about 8.5 to about 10.5; and
   (c) a second composition disposed in the second chamber, the second composition comprising an oxidizing agent and a non-ionic polyethylene oxide fatty alkyl ether surfactant, the second composition having a pH of from about 2.8 to about 3.8;
   wherein the container is not pressurized and each of the first composition and the second composition is maintained at atmospheric pressure, and wherein the oxidizing agent and the reducing agent are selected and being present in such proportion to provide a stoichiometric exothermic reaction and a drop in the pH of the first composition driving the release of carbon dioxide upon mixing of the first composition and the second composition.

13. The product of claim 12, wherein a stoichiometric mixture of the first composition and the second composition has a pH of from about 5 to about 7.

14. The product of claim 12, wherein a stoichiometric mixture of the first composition and the second composition has a pH of from about 6 to about 6.5.

15. The product of claim 12, wherein the container is not pressurized and each of the first composition and the second composition is maintained at atmospheric pressure.

16. A self-heating shaving product, comprising:
   (a) a container comprising a first chamber and a distinct second chamber;
   (b) a first composition disposed in the first chamber, the first composition being an oil-in-water emulsion comprising a reducing agent and a carbon dioxide source, the first composition having a pH of from about 8.5 to about 10.5; and
   (c) a second composition disposed in the second chamber, the second composition being an oil-in-water emulsion comprising an oxidizing agent, the second composition having a pH of from about 2.8 to about 3.8;
   wherein the oxidizing agent and the reducing agent are selected and being present in such proportion to provide a stoichiometric exothermic reaction and a drop in the pH of the first composition driving the release of carbon dioxide upon mixing of the first composition and the second composition.

* * * * *